United States Patent [19]

Monforte et al.

[11] Patent Number: 5,217,984

[45] Date of Patent: Jun. 8, 1993

[54] 1-PHENYL SUBSTITUTED-1H, 3H-THIAZOLE (3,4-A) BENZIMIDAZOLES AND PHARMACEUTICAL COMPOSITIONS CONTAINING THEM

[76] Inventors: Pietro Monforte; Anna M. Monforte; Maria Zappala; Giovanni Romeo; Silvana Grasso; Alba Chimirri, all of Dipartimento Farmaco-Chimico-Universitá Viale SS. Annunziata, 98168 Messina, Italy

[21] Appl. No.: 735,914

[22] Filed: Jul. 25, 1991

[30] Foreign Application Priority Data

Jul. 25, 1990 [IT] Italy .............................. 21063 A/90

[51] Int. Cl.$^5$ .................. A61K 31/425; C07D 513/04
[52] U.S. Cl. ..................................... 514/366; 548/151
[58] Field of Search ..................... 548/151; 514/366

[56] References Cited

U.S. PATENT DOCUMENTS 3,665,007  5/1972  Haugwitz et al. ................ 548/151
3,732,240  5/1973  Haugwitz et al. ................ 548/151
4,464,384  8/1984  Murase et al. .................... 548/151

FOREIGN PATENT DOCUMENTS 2056982  3/1981  United Kingdom .
2200116  7/1988  United Kingdom .

OTHER PUBLICATIONS

Chimirri et al., Synthesis, No. 3, pp. 244–246 (1988).
"An Unexpected Reaction Between 2,3-dihydro-2,2-,4-trimethyl-1H-1,5-benzo diazepine and Mercaptoacetic Acid", A. Chimirri et al., Chemical Abstracts, vol. 108, No. 9, Feb. 29, 1988, p. 680.

Primary Examiner—Joseph Paul Brust
Assistant Examiner—Mary Susan H. Gabilan
Attorney, Agent, or Firm—Oliff & Berridge

[57] ABSTRACT

1-Phenyl substituted-1H,3H-thiazole [3,4-a] benzimidazoles are prepared by reaction of o.phenilendiamine with a substituted benzaldehyde and with 2-mercaptoacetic acid. The new compounds are antiviral products.

12 Claims, 9 Drawing Sheets

1-PHENYL SUBSTITUTED-1H, 3H-THIAZOLE (3,4-A) BENZIMIDAZOLES AND PHARMACEUTICAL COMPOSITIONS CONTAINING THEM

The present invention is related to 1-phenyl substituted-1H,3H-thiazole [3,4-a] benzimidazoles, to a method for their preparation and to pharmaceutical compositions containing them.

The compounds of the invention have the following formula (I):

wherein each of $R_2$, $R_3$, $R_4$, $R_5$, and $R_6$, that can be the same or different, are selected from the group consisting of hydrogen, F, Cl, Br, hydroxy, $C_1-C_6$ alkyl, $C_1-C_6$ alkoxy, nitro, cyano, halo-$C_1-C_6$ alkyl, with the proviso that at least one of $R_2$, $R_3$, $R_4$, $R_5$, and $R_6$ is different from hydrogen.

Also the pharmaceutically acceptable salts as well as the single optical antipodes, i.e. the pure enantiomers, the racemates and mixtures thereof are included in the scope of the invention. The alkyl groups are branched or straight chain groups.

A halo-$C_1-C_6$ alkyl is preferably trihalo-$C_1-C_6$ alkyl group, in particular trifluoromethyl.

A $C_1-C_6$ alkyl group is preferably methyl.

A $C_1-C_6$ alkoxy group is preferably methoxy.

Preferred and representative compounds of the invention are:

(±) 1-(2-fluorophenyl)-1H,3H-thiazole [3,4-a] benzimidazole, (±) 1-(3-fluorophenyl)-1H,3H-thiazole [3,4-a] benzimidazole, (±) 1-(2-hydroxyphenyl)-1H,3H-thiazole [3,4-a] benzimidazole,

(±) 1-(2,6-difluorophenyl)-1H,3H-thiazole [3,4-a] benzimidazole, (±) 1-(2,6-dichlorophenyl)-1H,3H-thiazole [3,4-a] benzimidazole,

(±) 1-(2-chloro-6-fluorophenyl)-1H,3H-thiazole [3,4-a] benzimidazole, (±) 1-(2-nitro-5-chlorophenyl)-1H,3H-thiazole [3,4-a] benzimidazole.

The compounds of the invention of formula (I) are obtained by reaction of a mixture of 1,2-phenylendiamine and 2-mercaptoacetic acid with an aryl aldehyde of formula (II)

wherein $R_2$, $R_3$, $R_4$, $R_5$, and $R_6$ are as above defined, in an inert solvent, according to the following reaction scheme:

In accordance with the above mentioned "one pot reaction" process, the reaction is carried out by treatment of equimolar amounts of an aryaldehyde (II) and of 1,2-phenylendiamine with a molar excess of 2-mercaptoacetic acid in a inert solvent.

Suitable solvents are amides as dimethylformamide, dimethylacetamide; cyclic or linear ethers such as anisole, dimethoxyethane, dioxane, tetrahydrosulfoxide; esters such as ethyl acetate, ethyl formate; halogenated hydrocarbons such as carbonium tetrachloride, chloroform, methylene dichloride, 1,2-dichloroethane; aliphatic hydrocarbons such as n-hexane, n-heptane; cycloaliphatic hydrocarbons such as cyclohexane, aromatic hydrocarbons such as benzene, toluene, pyridine as well as mixture thereof.

The reaction may be carried out at temperatures ranging from room temperature to about the reflux temperature of the inert solvent, preferably from about 40° C. to 100° C. and more preferably from 75° to 85° C.

The reaction time ranges from few hours to three days and more, but usually do not exceed two days, when it is carried out in benzene at 80° C.

The arylaldehydes of formula (II) are known substances that can be prepared using known methods (see Beilstein collection as reference book) and/or are commercially available. The easy availability of aryl aldehydes of formula (II) makes the "one pot reaction" procedure to be an advantageous and valid alternative in the synthesis of the compounds of the formula (I) of the present invention in respect to other methods involving substituted benzimidazoles as starting material in thiazole ring cyclization by reaction with suitable sulfur compounds.

During the one pot reaction and according to the above mentioned reaction scheme, the intermediate formation of mono-azomethine compounds of formula (III)

and that of 2-aryl-3-(2-aminophenyl)-thiazolidin-3H(4)-ones of formula (IV)

is supposed to occur.

The compounds of the invention are then formed by further internal cyclization of the compounds of formula (IV), substantially in accordance with the reaction mechanism already disclosed in *Synthesis*, 244-246 (1988).

Bis-azomethine compounds of formula (V)

are sometimes undesired by-products whose formation may be reduced by suitable selection of reagent molecular ratio and/or reaction time.

GENERAL OPERATIVE CONDITIONS

To a solution of 50 mmoles of o-phenylenediamene in 100 ml of anhydrous benzene add 50 mmoles of suitable aldehyde and 100 mmoles of mercaptoacetic acid.

The reactive mixture is then heated under reflux for different lengths of time (see Tab. 1). When the reaction is terminated the whole of the mixture is washed several times using a 2% solution of $Na_2CO_3$ to eliminate the excess acid.

By distilling the solvent at a low pressure, an oily residue is obtained which is usually cristallyzed using ether or purified cromatographically.

The starting products in the process according to the present invention are easily found on the market and are not expensive.

Analytical Methods for Determining the Chemical-Physical Characteristics of the Compounds The melting points were found using a Kofler device and are not corrected.

Elementary analysis was carried out using a Carlo Erba mod.

1106 Elemental Analyser and the values found were between ±0.4% of the theoretical values.

The course of the reactions and the purity of the compounds was controlled by using the thin layer chromatography (Kieselgel 60 F254 Merck), with a mixture of ether/petroleum ether (8:2) as the eluent.

The 'H-R.M.N. spectra were registered using a Bruker WP 80 SY spectometer. The chemical shifts are expressed in δ (ppm) and the coupling costants (J) in Hz.

The spectra of all the compounds were registered in either a $CDCl_3$ or DMSO-d6 solution.

The chemical and physical characteristics of some of the synthesized products are given in Table 1 and the respective structures agree both with the elementary and spectroscopic analytical data.

MEASURE OF LIPOPHYLIA

The lipophylic character of the synthesized compounds was evaluated with reverse phase, thin layer chromatography.

The non-polar stationary phase is represented by plates of Merck 60 $F_{254}$ silanized silica gel, whereas the polar phase consists of an acetone/water mixture (2:1).

The compounds were solubilized in chloroform (3 mg/ml).

The $R_M$ values were calculated from the average experimental values of $R_F$, obtained from three chromatograms using the formula:

$$R_M = \log(1/R_F) - 1.$$

Higher values of $R_M$ corresponding to lower values of $R_F$ indicate more lipophylic compounds.

The relative lipophylia ($R_M$) of the synthesized compounds is given in Table 1.

TABLE 1

Substituted 1H, 3H-thiazole [3,4-a] Benzimidazoles

| Comp. | R | TIME REACTION h | YIELD | M.P.* | Formula | $R_M$ | 'H-R.M.H. |
|---|---|---|---|---|---|---|---|
| I | 2-Br—$C_6H_4$ | 46 | 17 | 127-130 | $C_{15}H_{11}BrH_2S$ | −0,410 | 4,29 e 4,42(dd, 2H, J=14,6 $CH_2$); 6,79-7.79(m, 9H, ArH e CH). |
| II | 3-Br—$C_6H_4$ | 45 | 25 | 155-157 | $C_{15}H_{11}BrH_2S$ | −0,406 | 4,33 e 4,47(dd, 2H, J=14,74, $CH_2$); 6,33(s, 1H, CH); 6,70-7,78(m, 8H, ArH). |
| III | 4-Br—$C_6H_4$ | 48 | 25 | 139-142 | $C_{15}H_{11}BrH_2S$ | −0,430 | 4,34 e 4,45(dd, 2H, J=14,8, $CH_2$); 6.41(s 1H, CH); 6,66– |

TABLE 1-continued

Substituted 1H, 3H-thiazole [3,4-a] Benzimidazoles

| Comp. | R | TIME REACTION h | YIELD | M.P.° | Formula | $R_M$ | ¹H-R.M.H. |
|---|---|---|---|---|---|---|---|
| IV | 2-F—$C_6H_4$ | 48 | 18 | 118–121 | $C_{15}H_{11}FN_2S$ | −0,468 | 4,30 e 4,48(dd, 2H, J=14,6, $CH_2$); 6,74(sa, 1H, CH); 6,81–7,77(m, 8H, .rH). |
| V | 3-F—$C_6H_4$ | 48 | 21 | 125–129 | $C_{15}H_{11}FN_2S$ | −0,434 | 4,37 e 4,49(dd, 2H, J=14,6, $CH_2$); 6,46(s, 1H, CH); 6,72–7,78(m, 8H, ArH). |
| VI | 4-F—$C_6H_4$ | 40 | 16 | 140–142 | $C_{15}H_{11}FN_2S$ | −0,412 | 4,36 e 4,46(dd, 2H, J=14,8, $CH_2$); 6,46(s, 1H, CH); 6,65–7,77(m, 8H ArH). |
| VII | 2-Cl—$C_6H_4$ | 24 | 24 | 124–126 | $C_{15}H_{11}ClN_2S$ | −0,393 | 4,34 e 4,45(dd, 2H, J=14,7, $CH_2$); 6,40(s, 1H, CH); 6,60–7,76(m, 8H ArH). |
| VIII | 3-Cl—$C_6H_4$ | 24 | 32 | 130–132 | $C_{15}H_{11}ClN_2S$ | −0,428 | 4,32 e 4,46(dd, 2H, J=14,7, $CH_2$); 6,37(s, 1H, CH); 6,69–6,76(m, 8H ArH). |
| IX | 4-Cl—$C_6H_4$ | 8 | 18 | 136–138 | $C_{15}H_{11}ClN_2S$ | −0,402 | 4,36 e 4,47(od, 2H, J=14,7, $CH_2$); 6,45(sa, 1H, CH); 6,54–7,77(m, 8H ArH). |
| X | 2-$CH_3$—$C_6H_4$ | 48 | 40 | 181–183 | $C_{16}H_{14}N_2S$ | −0,452 | 2,37(s, 3H, $CH_3$); 4,38 e 4,44(dd, 2H, J=14,7, $CH_2$); 6,69(s, 1H, CH); 6,77–7,79 (m, 8H ArH). |
| XI | 3-$CH_3$—$C_6H_4$ | 48 | 32 | 146–148 | $C_{16}H_{14}N_2S$ | −0,399 | 2,32(s, 3H, $CH_3$); 4,38 e 4,49(dd, 2H, J=14,8, $CH_2$) 6,45(s, 1H, CH); 6,70–7,77 (m, 8H ArH). |
| XII | 3-$OCH_3$—$C_6H_4$ | 48 | 20 | 131–134 | $C_{16}H_{14}N_2OS$ | −0,436 | 3,74(s, 3H, $OCH_3$); 4,38 e 4,48(dd, 2H, J=14,9, $CH_2$); 6,45(s, 1H, CH); 6,64–7,75 (m, 8H ArH). |
| XIII | 4-$OCH_3$—$C_6H_4$ | 26 | 20 | 54–55 | $C_{16}H_{14}N_2OS$ | −0,477 | 3,80(s, 3H, $OCH_3$); 4,37 e 4,46(dd, 2H, J=14,9, $CH_2$); 6,49(s, 1H, CH); 6,68–8,12 (m, 8H ArH). |
| XIV | 2-$CF_3$—$C_6H_4$ | 26 | 42 | 169–171 | $C_{16}H_{11}F_3N_2S$ | −0,349 | 4,35 e 4,49(dd, 2H, J=14,6, $CH_2$); 6,68–7,79(m, 9H Arh e CH). |
| XV | 3-$CF_3$—$C_6H_4$ | 24 | 30 | 166–168 | $C_{16}H_{11}F_3N_2S$ | −0,378 | 4,37 e 4,50(dd, 2H, J=14,6, $CH_2$); 6,49(s, 1H, CH); 6,64–7,78(m, 8H ArH). |
| XVI | 4-$CF_3$—$C_6H_4$ | 30 | 38 | 170–172 | $C_{16}H_{11}F_3N_2S$ | −0,387 | 4,40 e 4,51(dd, 2H, J=14,8, $CH_2$); 6,53(s, 1H, CH); 6,68–7,78(m, 8H ArH). |
| XVII | 3-OH—$C_6H_4$ | 48 | 13 | 240–242 | $C_{15}H_{12}N_2OS$ | −0,591 | 4,40 e 4,56(dd, 2H, J=14,9, $CH_2$); 6,69–7,66(m, 9H ArH e CH); 9,52(s, 1H, OH). |
| XVIII | 4-CN—$C_6H_4$ | 48 | 16 | 146–148 | $C_{16}H_{11}N_3S$ | −0,506 | 4,38 e 4,49(dd, 2H, J=14,8, $CH_2$); 6,50(s, 1H, CH); 6,66–7,87(m, 8H ArH). |
| XIX | 2,3-$F_2$—$C_6H_3$ | 48 | 31 | 109–111 | $C_{15}H_{10}F_2N_2S$ | −0,452 | 4,32 e 4,49(dd, 2H, J=14,6, $CH_2$); 6,72–7,78(m, 8H ArH e CH). |
| XX | 2,4-$F_2$—$C_6H_3$ | 48 | 17 | 135–137 | $C_{15}H_{10}F_2N_2S$ | −0,452 | 4,32 e 4,49(dd, 2H, J=14,6, $CH_2$); 6,72–7,78(m, 8H ArH e CH). |
| XII | 2,5-$F_2$—$C_6H_3$ | 50 | 23 | 103–105 | $C_{15}H_{10}F_2N_2S$ | −0,432 | 4,35 e 4,52(dd, 2H, J=14,6, $CH_2$); 6,65–7,80(m, 8H ArH e CH). |
| XXII | 2,6-$F_2$—$C_6H_3$ | 48 | 52 | 140–142 | $C_{15}H_{10}F_2N_2S$ | −0,475 | 4,30 e 4,57(dd, 2H, J=14,3, $CH_2$); 6,73–7,75(m, 8H ArH e CH). |
| XXIII | 3,4-$F_2$—$C_6H_3$ | 48 | 44 | 141–143 | $C_{15}H_{10}F_2N_2S$ | −0,430 | 4,35 e 4,47(dd, 2H, J=14,8, $CH_2$); 6,41(s, 1H, CH); 6,68–7,78(m, 7H ArH). |
| XXIV | 2,3-$Cl_2$—$C_6H_3$ | 48 | 23 | 126–128 | $C_{15}H_{10}Cl_2N_2S$ | −0,355 | 4,29 e 4,41(dd, 2H, J=14,9, $CH_2$); 6,56–7,80(m, 8H ArH e |

TABLE 1-continued

Substituted 1H, 3H-thiazole [3,4-a] Benzimidazoles

| Comp. | R | TIME REACTION h | YIELD | M.P.° | Formula | $R_M$ | 'H-R.M.H. |
|---|---|---|---|---|---|---|---|
| XXV | 2,4-Cl$_2$—C$_6$H$_3$ | 48 | 23 | 105–107 | C$_{15}$H$_{10}$Cl$_2$N$_2$S | −0,329 | 4,28 e 4,40(dd, 2H, J=14,9 CH$_2$); 6,69–7,79(m, 8H ArH e CH). |
| XXVI | 2,6-Cl$_2$C$_6$H$_3$ | 48 | 21 | 194–196 | C$_{15}$H$_{10}$Cl$_2$N$_2$S | −0,402 | 4,41 e 4,50(dd, 2H, J=14,4, CH$_2$); 6,70–7,75(m, 8H ArH e CH). |
| XXVII | 3,4-Cl$_2$—C$_6$H$_3$ | 48 | 38 | 89–90 | C$_{15}$H$_{10}$Cl$_2$N$_2$S | −0,362 | 4,35 e 4,48(dd, 2H, J=14,8, CH$_2$); 6,39(s, 1H, CH); 6,70–7,78(m, 7H ArH). |
| XXVIII | 3,5-Cl$_2$—C$_6$H$_3$ | 48 | 11 | 174–176 | C$_{15}$H$_{10}$Cl$_2$N$_2$S | −0,337 | 4,34 e 4,50(dd, 2H, J=14,7, CH$_2$); 6,36(s, 1H, CH); 6,74–7,79(m, 7H ArH). |
| XXIX | 2-Cl-6-F—C$_6$H$_3$ | 48 | 27 | 144–145 | C$_{15}$H$_{10}$ClFN$_2$S | −0,452 | 4,35 e 4,56(dd, 2H, J=14,3, CH$_2$); 6,85–7,76(m, 8H ArH e CH). |
| XXX | 2-Cl-5-NO$_2$—C$_6$H$_3$ | 48 | 38 | 178–180 | C$_{15}$H$_{10}$ClN$_3$O$_2$S | −0.423 | 4,36 e 4,51(dd, 2H, J=14,6, CH$_2$); 6,77–8,18(m, 8H ArH e CH). |
| XXXI | 3-NO$_2$-4-Cl—C$_6$H$_3$ | 48 | 11 | 102–104 | C$_{15}$H$_{10}$ClN$_2$O$_2$S | −0,414 | 4,38 e 4,51(dd, 2H, J=14,7, CH$_2$); 6,49(s, 1H, CH); 6,70–7,89(m, 7H ArH). |
| XXXII | 2-NO$_2$-5-Cl—C$_6$H$_3$ | 48 | 10 | 158–160 | C$_{15}$H$_{10}$ClN$_3$O$_2$S | −0,387 | 4,26 e 4,43(dd, 2H, J=14,8, CH$_2$); 6,69–8,23(m, 8H ArH e CH). |

Using in the general procedure above described an arylaldehyde selected from the group consisting of 3-cyano, ortho, meta and/or para nitro, ortho or para hydroxy, 2-methoxy, 3-nitro-4-hydroxy, 3-chloro-4-fluoro, 2,3,6-trichloro, 2,3,4-trifluoro, 2,3,5-trichloro, 2,3,5,6-tetrafluoro; 2,3,4,5,6-pentafluoro; 3,5-ditrifluoromethyl; 3,4,5-trimethoxy; 3,5-dimethoxy-4-hydroxy, 2,4,6-trimethoxy; 2-nitro-4,5-dimethoxy; 2,3-dimethyl-4-methoxy; 3-methoxy-4-hydroxy-5-bromo-benzaldehyde, the following compounds are prepared:

| | |
|---|---|
| 1-(3-cyano-phenyl)-1H,3H-thiazole [3,4-a] benzimidazole   m.p. 123–125° C. | (XXXIII) |
| 1-(2-hydroxy-phenyl)-1H,3H-thiazole [3,4-a] benzimidazole | (XXXIV) |
| 1-(4-hydroxy-phenyl)-1H,3H-thiazole [3,4-a] benzimidazole | (XXXV) |
| 1-(2-nitro-phenyl)-1H,3H-thiazole [3,4-a] benzimidazole   m.p. 150–152° C. | (XXXVI) |
| 1-(3-nitro-phenyl)-1H,3H-thiazole [3,4-a] benzimidazole   m.p. 180–181° C. | (XXXVII) |
| 1-(4-nitro-phenyl)-1H,3H-thiazole [3,4-a] benzimidazole   m.p. 148–149° C. | (XXXVIII) |
| 1-(2-methoxy-phenyl)-1H,3H-thiazole [3,4-a] benzimidazole | (XXXIX) |
| 1-(3-nitro-4-hydroxy-phenyl)-1H,3H-thiazole [3,4-a] benzimidazole | (XL) |
| 1-(3-chloro-4-fluoro-phenyl)-1H,3H-thiazole [3,4-a] benzimidazole   m.p. 108–110° C. | (XLI) |
| 1-(2,3,6-trichloro-phenyl)-1H,3H-thiazole [3,4-a] benzimidazole | (XLII) |
| 1-(2,3,4-trifluoro-phenyl)-1H,3H-thiazole [3,4-a] benzimidazole | (XLIII) |
| 1-(2,3,5-trichloro-phenyl)-1H,3H-thiazole [3,4-a] benzimidazole | (XLIV) |
| 1-(2,3,5,6-tetrafluoro-phenyl)-1H,3H-thiazole [3,4-a] benzimidazole | (XLV) |
| 1-(2,3;4,5,6-pentafluoro-phenyl)-1H,3H-thiazole [3,4-a] benzimidazole | (XLVI) |
| 1-(3,5-ditrifluoro-methyl9-1H,3H-triazole [3,4-a] benzimidazole   m.p. 175–177° C. | (XLVII) |
| 1-(3,4,5-trimethoxy-phenyl)-1H,3H-thiazole [3,4-a] benzimidazole | (XLVIII) |
| 1-(3,5-dimethoxy-4-hydroxy-phenyl)-1H,3H-thiazole [3,4-a] benzimidazole | (XLIX) |
| 1-(2,4,6-trimethoxy-phenyl)-1H,3H-thiazole [3,4-a] benzimidazole | (L) |
| 1-(2-nitro-4,5-dimethoxy-phenyl)-1H,3H-thiazole [3,4-a] benzimidazole | (LI) |
| 1-(2,3-dimethyl-4-methoxy-phenyl)-1H,3H-thiazole [3,4-a] benzimidazole | (LII) |
| 1-(3-methoxy-4-hydroxy-5-bromo-phenyl)-1H,3H-thiazole [3,4-a] benzimidazole | (LIII) |

The compounds of the invention of the formula (I) are HIV-1 reverse transcriptase inhibitors of new structure, characterized by favourable therapeutic indexes.

For their effects on HIV-induced cytopathogenicity in human T$_4$-lymphocyte cell line (CEM), the compounds of the present invention were evaluated according to NIH procedures as described by R. Vince et al., Biochem. Biophys.Res.Comm., 156, 1046, 1988 and by O. S. Weislow et al. J. Natl.Canc. Inst., 81. 577,1988.

It was possible to evaluate for many compounds of the invention:

a) the effective concentration 50% (EC$_{50}$), which represents the concentration of the tested compound resulting in 50% reduction of the viral cytopathic effect.

b) the inhibitory concentration 50% (IC$_{50}$) which represents the toxic concentration of drug resulting in 50% growth inhibition of normal uninfected cells.

c) the therapeutic index TI$_{50}$ which is determined as the IC$_{50}$/EC$_{50}$ ratio.

Only substances able to cause at least a 50% or greater reduction of viral cytopathic effect are kept in consideration for further investigation.

The methods, the test conditions, the evaluation criteria of the anti-HIV activity in vitro are described by Weislow, O. W., Kieser, R., Fine, D., Bader, J., Shoemaker, R. H., Boyd, M. R.: New soluble-formazan assay for HIV-1 cytopathic effects: application to high-flux screening of synthetic and natural products for AIDS-antiviral activity. J. Nati, Cancer Inst. 81:577-586,1989.

The results of the test for some compounds of the invention are given in the following Table 2.

TABLE 2

| COMPOUND | | IC$_{50}$(10$^{-6}$M) | EC$_{50}$(10$^{-6}$M) | TI$_{50}$ |
|---|---|---|---|---|
| IV | (2-fluoro-phenyl) | >126 | 7.63 | >16.5 |
| V | (3-fluoro-phenyl) | 67.4 | 5.74 | 11.8 |
| XVII | (3-hydroxy-phenyl) | 127 | 114 | 1.11 |
| XXII | (2,6-difluoro-phenyl) | 80 | 1.0 | 80 |
| XXVI | (2,6-dichloro-phenyl) | 22.3 | 0.257 | 86.8 |
| XXIX | (2-chloro-6-fluoro-phenyl) | 19.6 | 0.596 | 32.8 |
| XXX | (2-chloro-5-nitro-phenyl) | >54.4 | 15.9 | >3.42 |
| XXXIII | (3-cyano-phenyl) | 38.3 | 2.94 | 13.1 |
| XXXVI | (2-nitro-phenyl) | 37.2 | 17.2 | 2.16 |

The tested compounds inhibit the reverse transcriptase of HIV-1 but not of HIV-2.

They inhibit p 24 and infectious virus production.

The above compounds tested for toxicity did not induce lethality in mice at doses up to 10 ml/kg i.v.

In men treated with 5% solutions in water, 0.5 mg/kg/day i.v., no adverse effect was observed.

Some diagrams relevant to the in vitro antiviral activity of the compounds according to the invention are reported hereinafter.

On the left of the diagrams of FIG. 1 to FIG. 7 the percentage of the untreated control culture is reported: on the right side the percentage of protection is reported.

Figure 1:
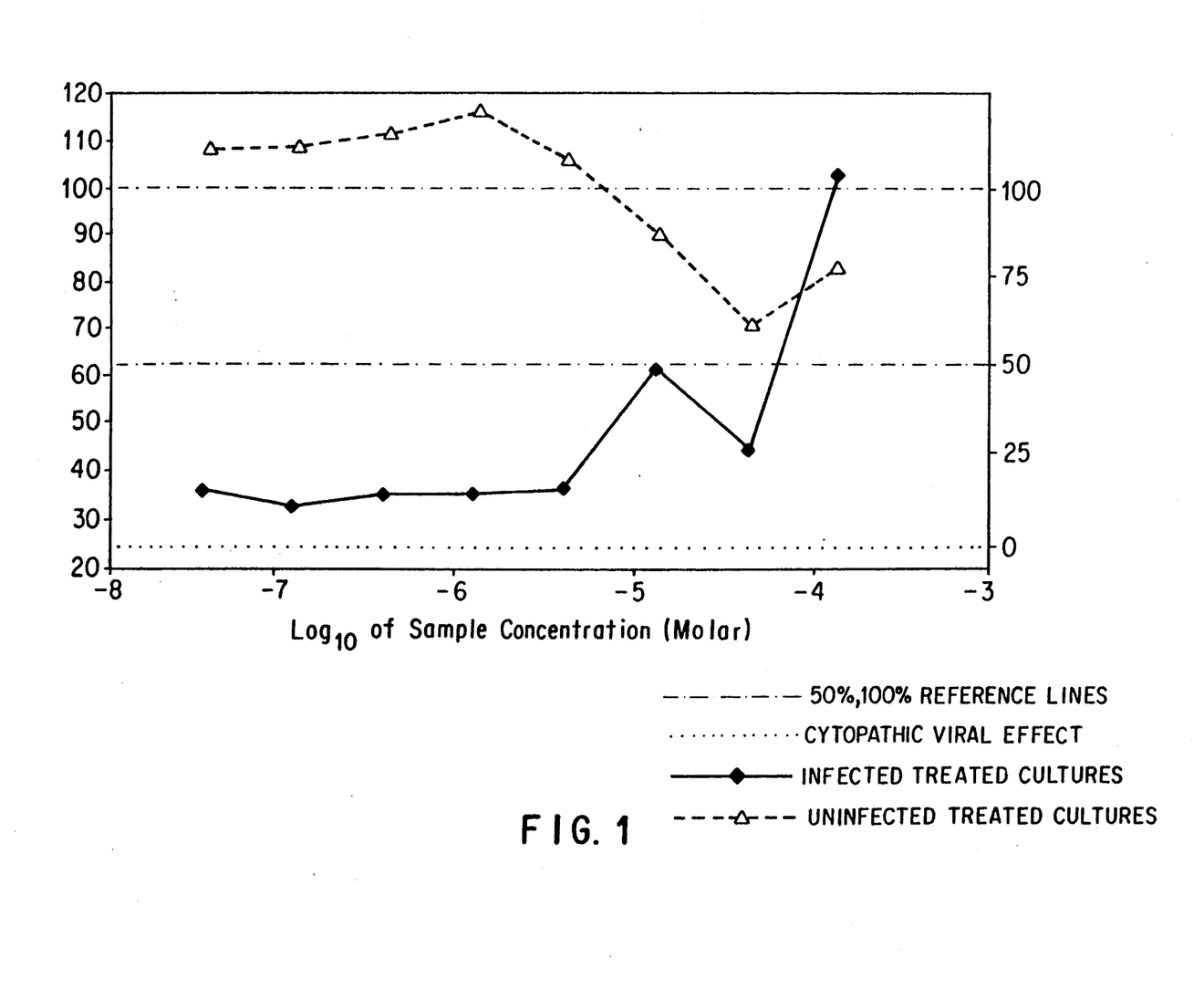
FIG. 1 is a diagram showing in vitro antiviral activity of compound IV.
Figure 2:
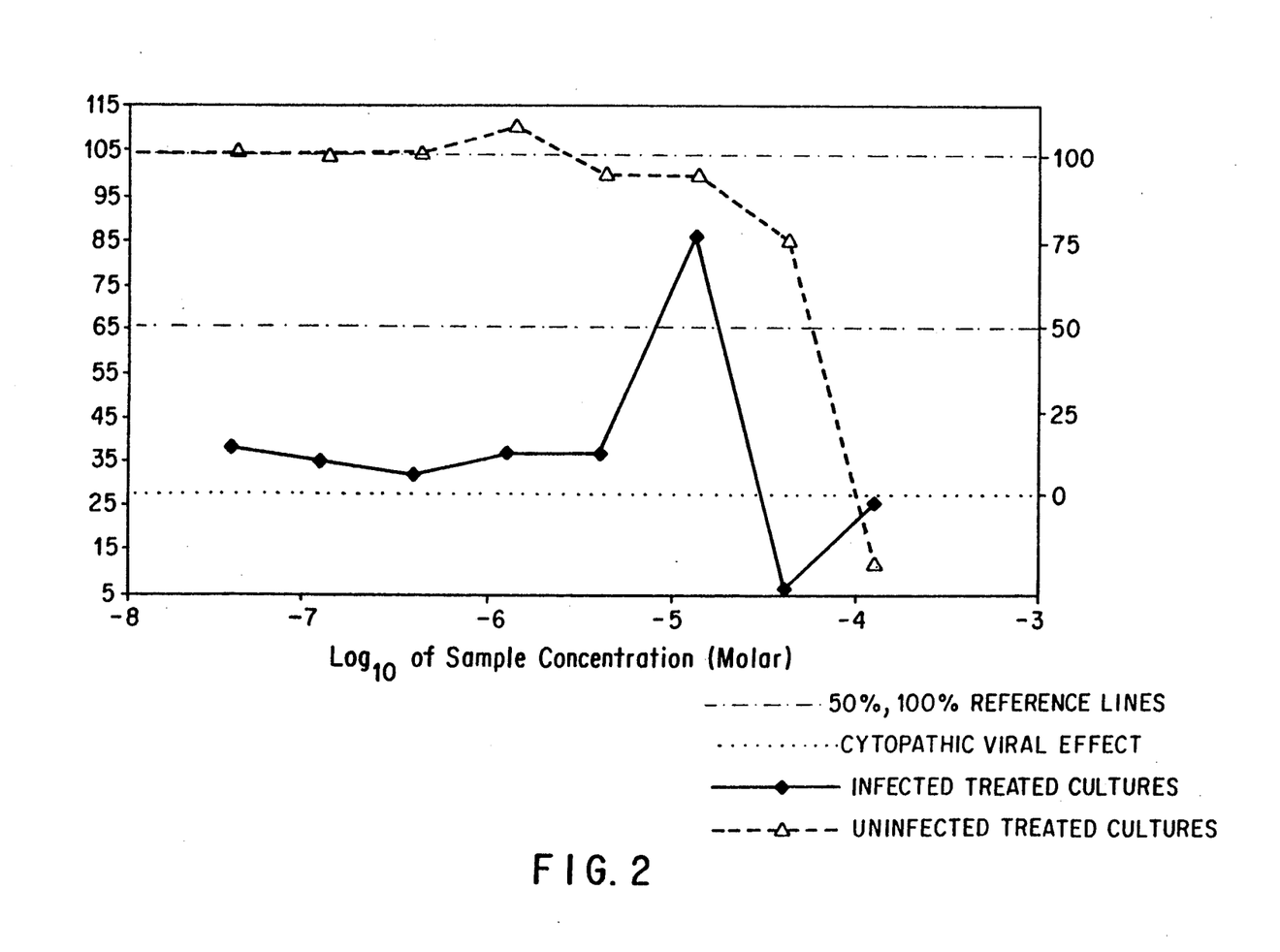
FIG. 2 is a diagram showing in vitro antiviral activity of compound V.
Figure 3:
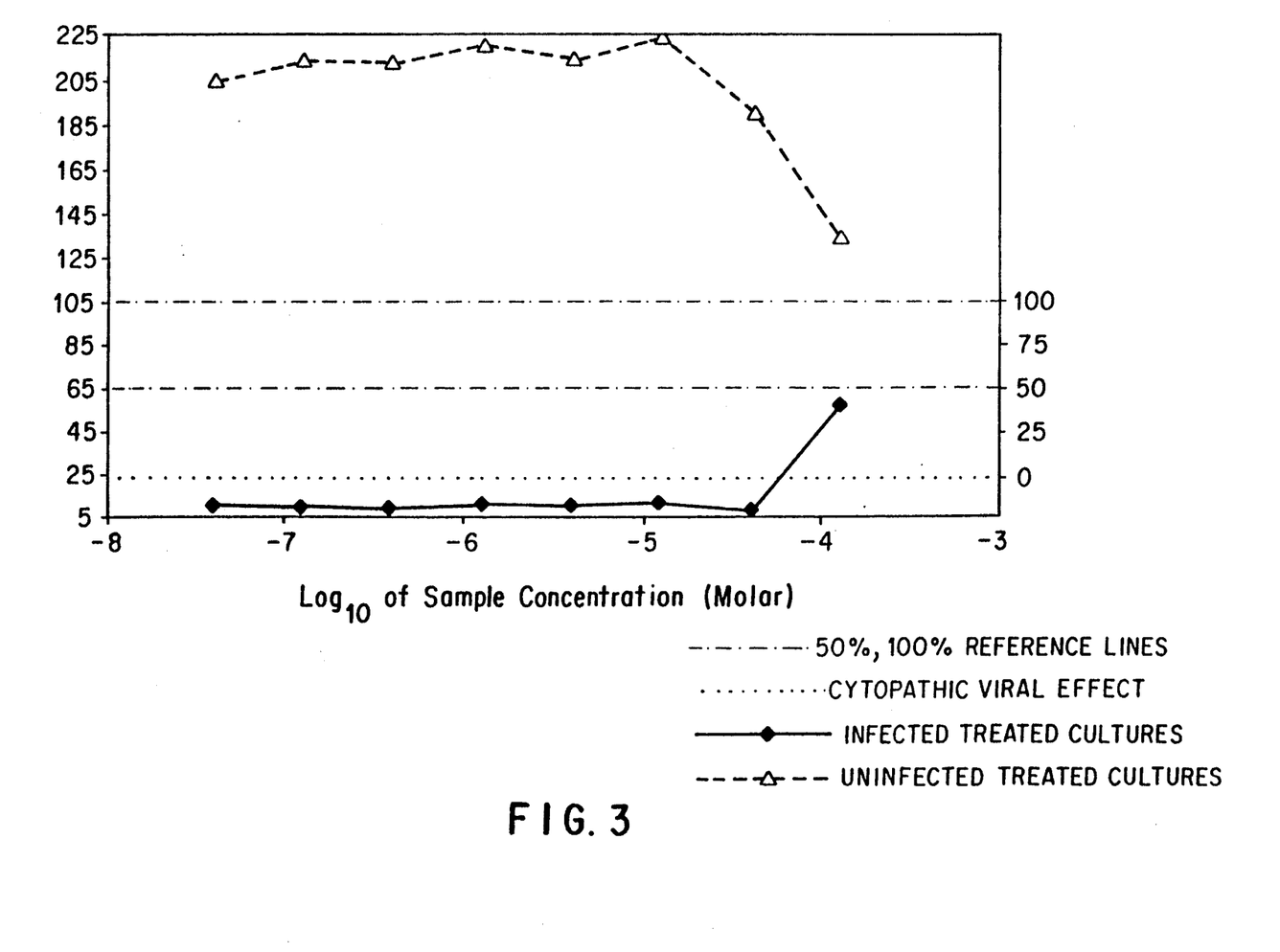
FIG. 3 is a diagram showing in vitro antiviral activity of compound XVII.
Figure 4:
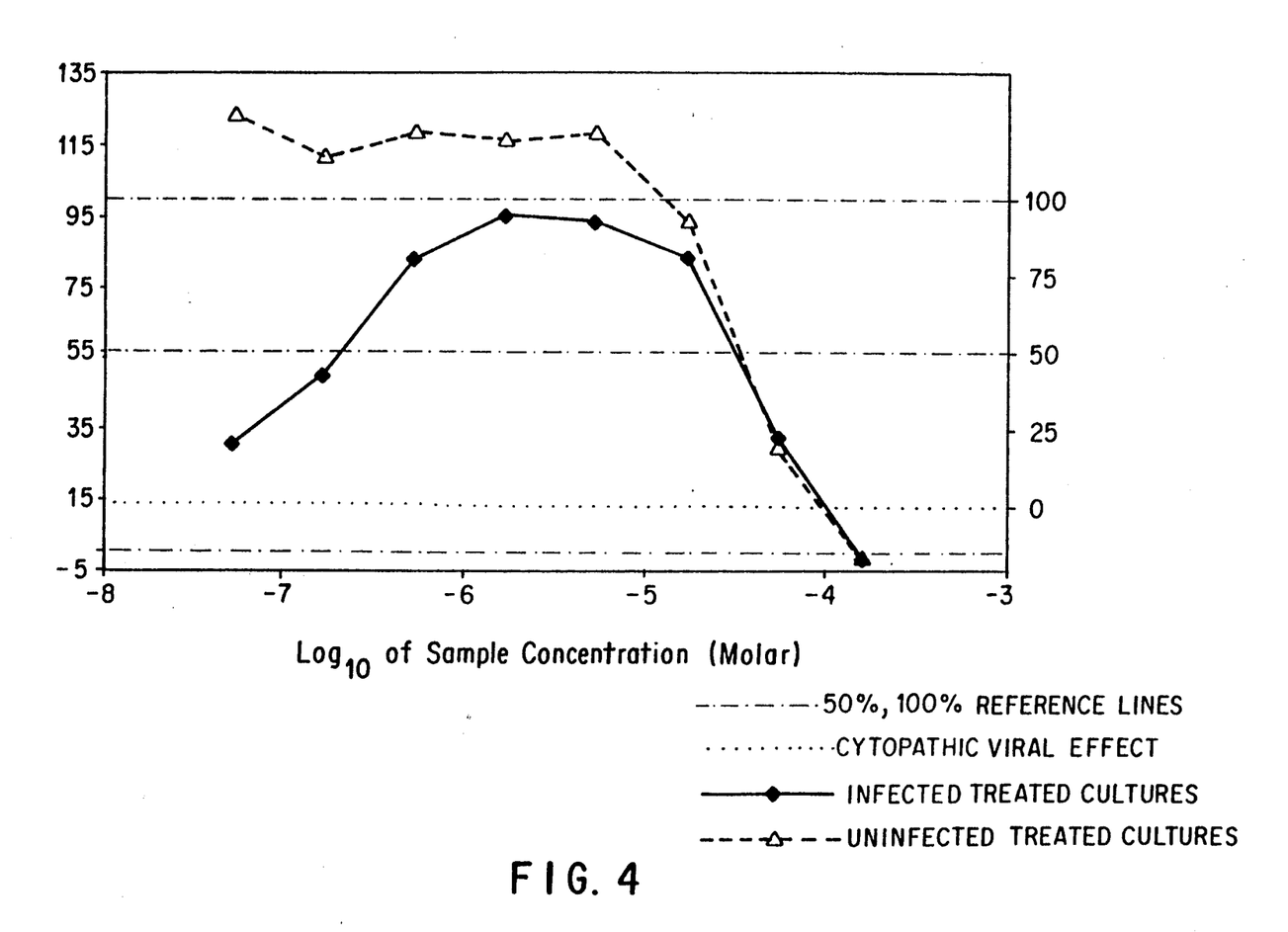
FIG. 4 is a diagram showing in vitro antiviral activity of compound XXII.
Figure 5:
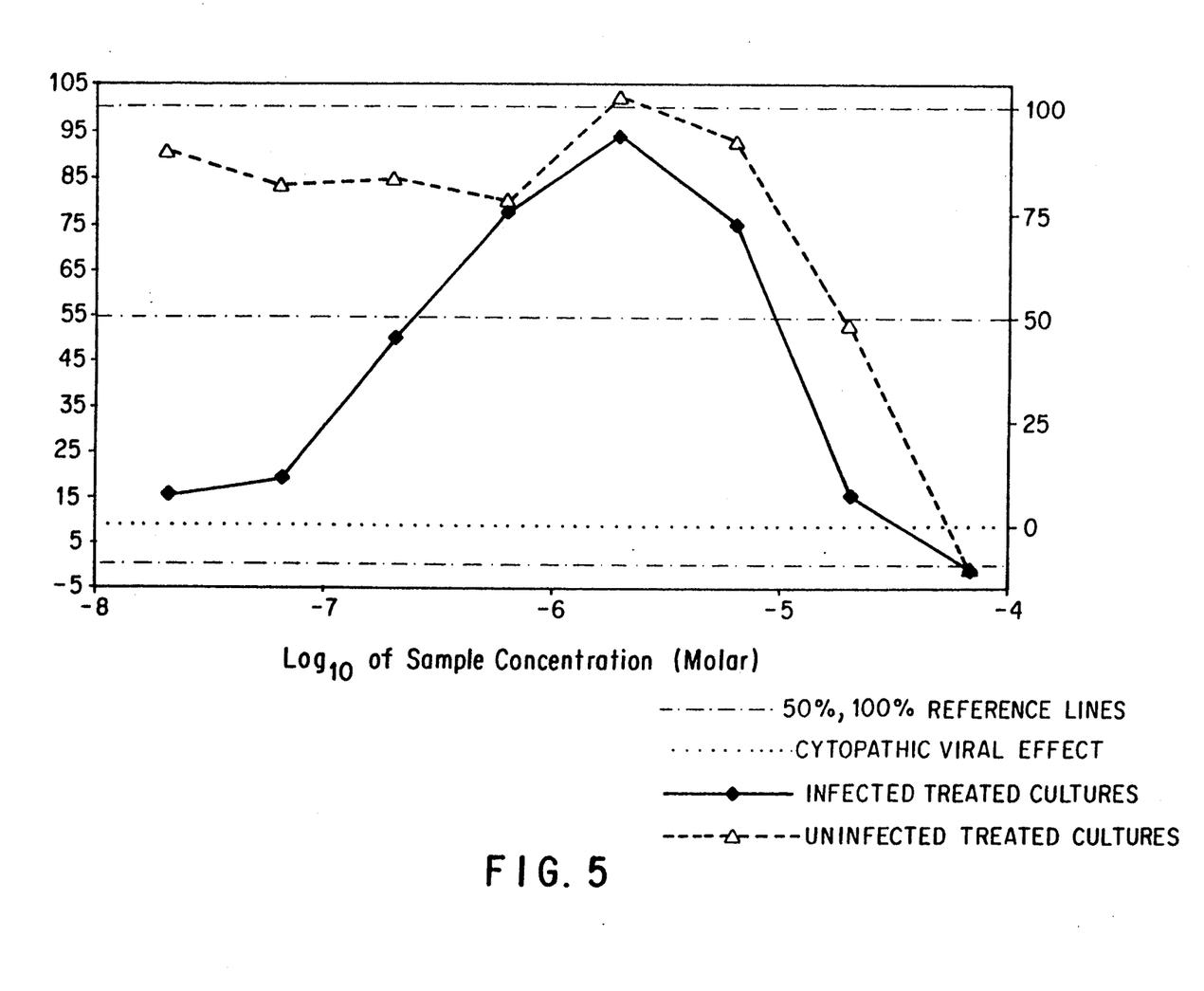
FIG. 5 is a diagram showing in vitro antiviral activity of compound XXVI.
Figure 6:
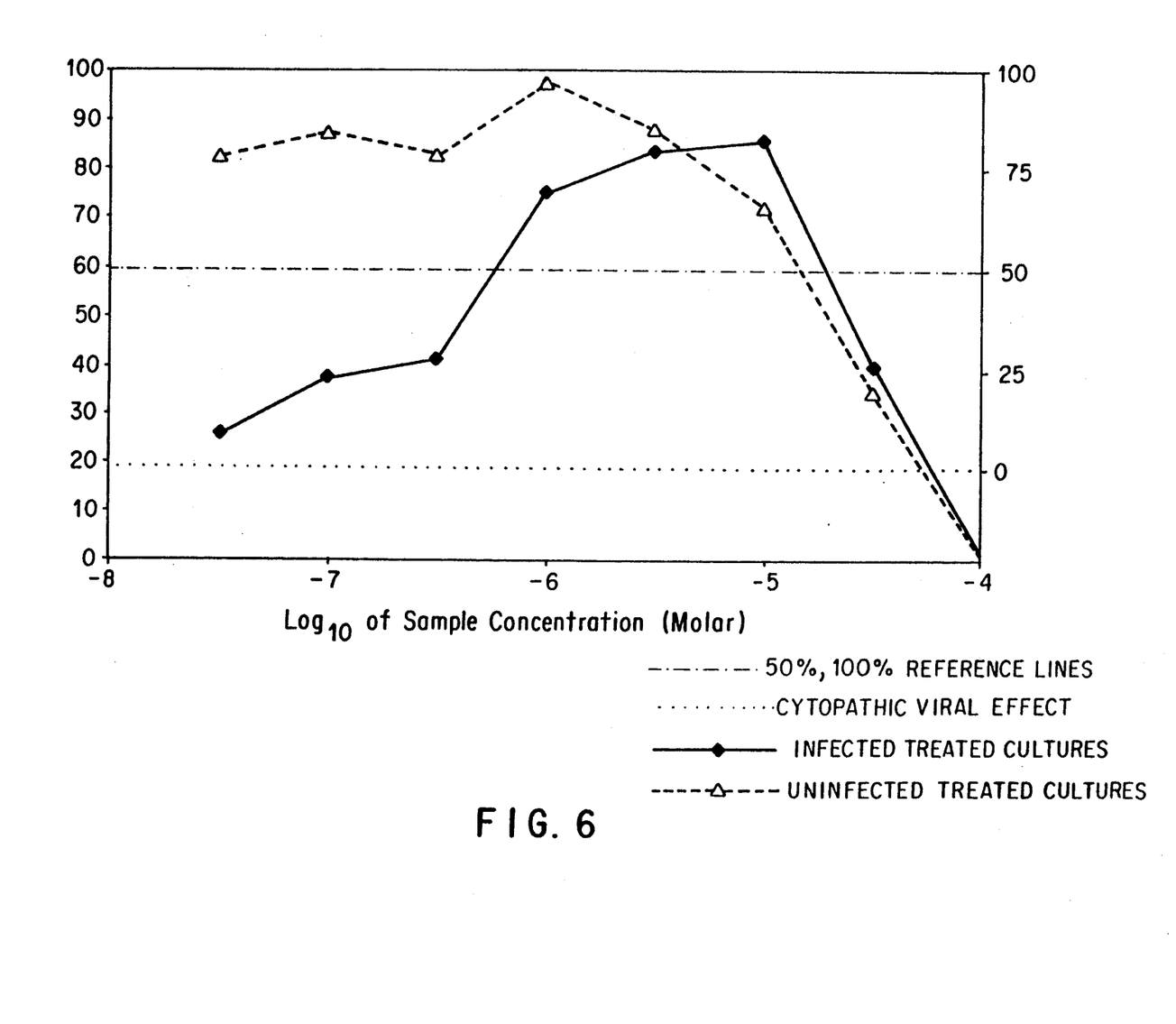
FIG. 6 is a diagram showing in vitro antiviral activity of compound XXIX.
Figure 7:
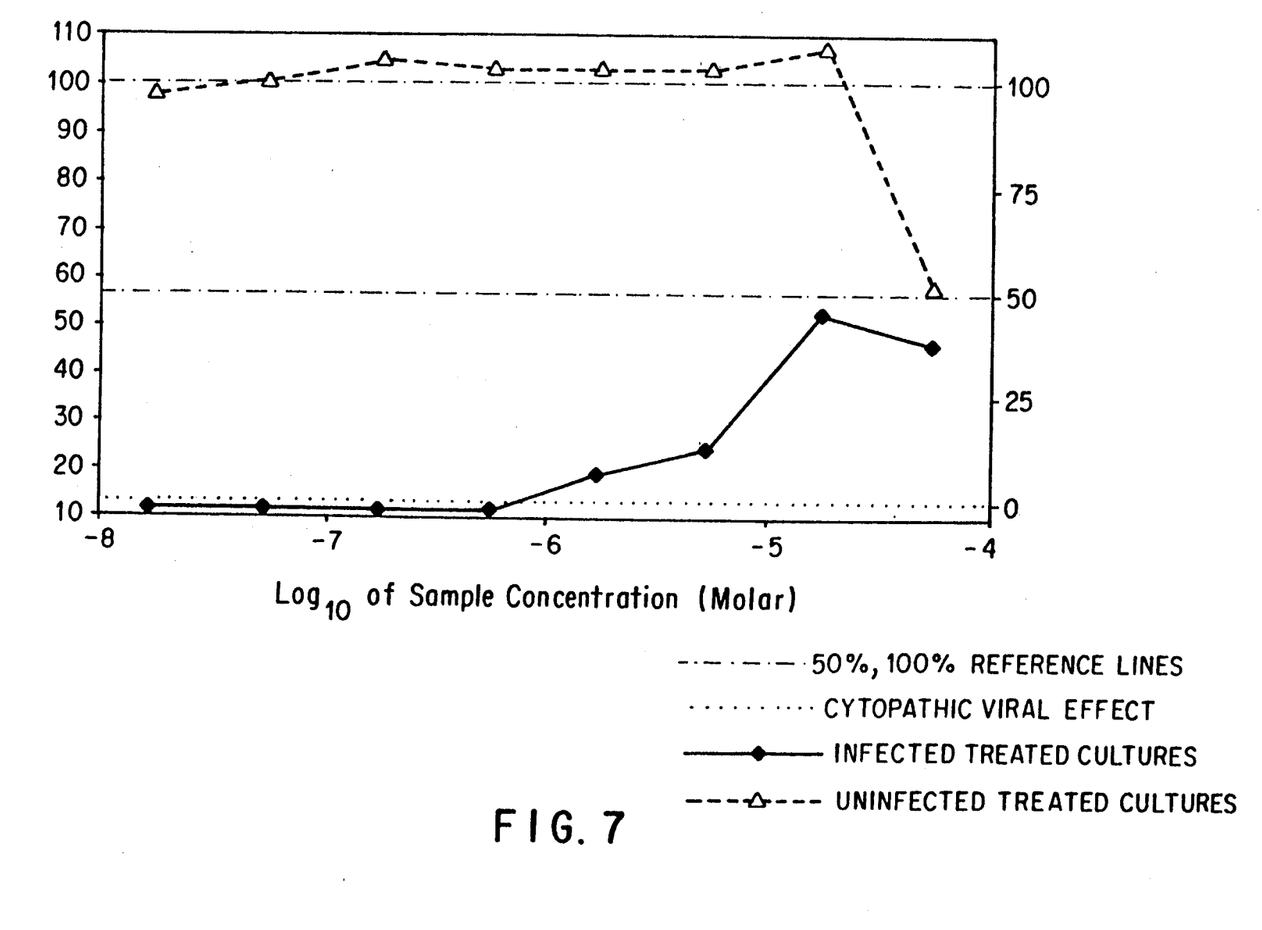
FIG. 7 is a diagram showing in vitro antiviral activity of compound XXX.
Figure 8:
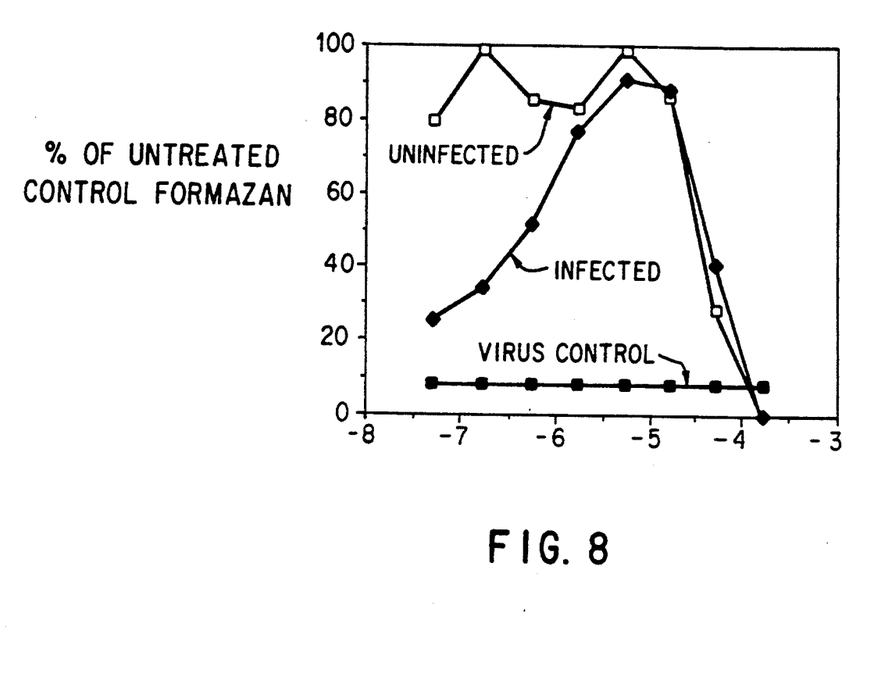
FIGS. 8-11 are diagrams showing antiviral activity of compound XXII.
Figure 9:
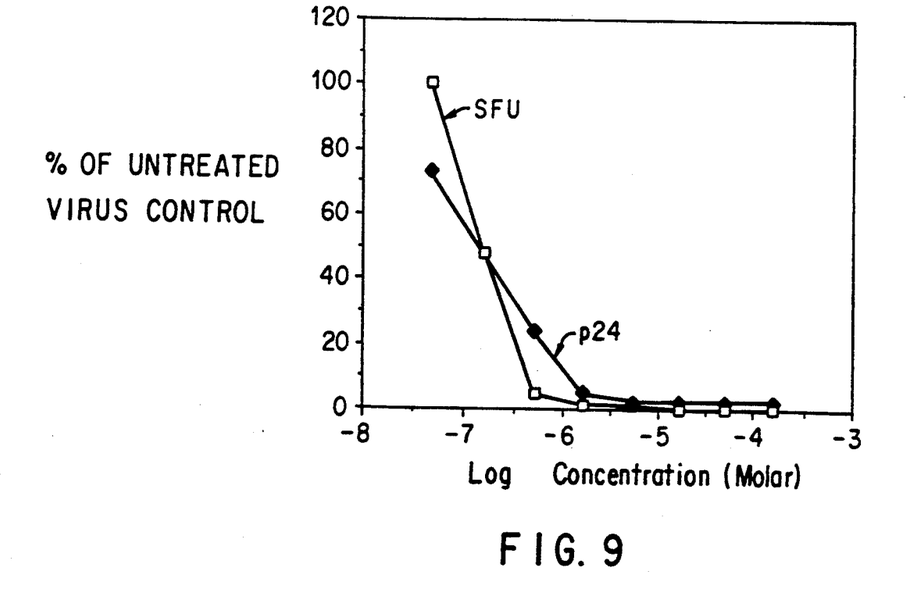
Figure 10:
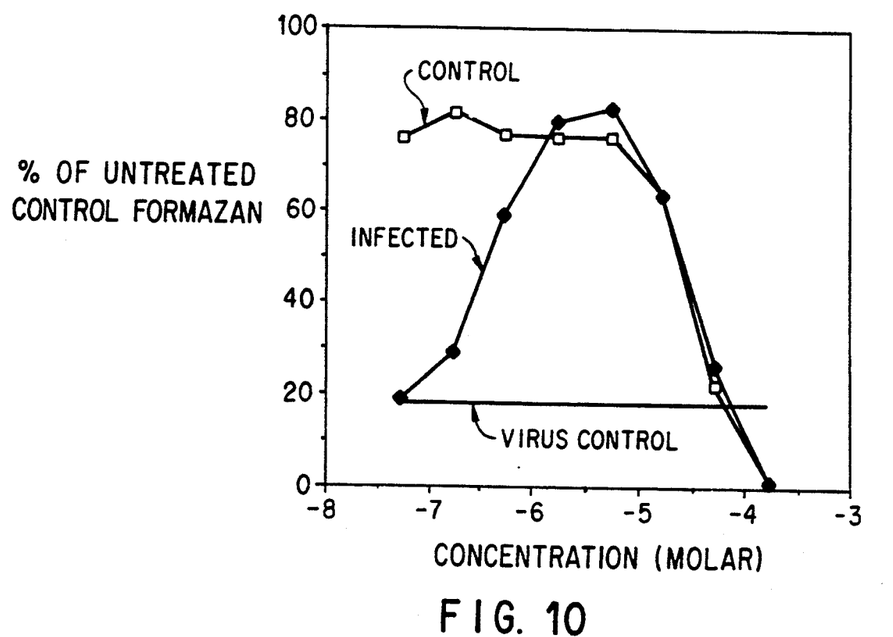
Figure 11:
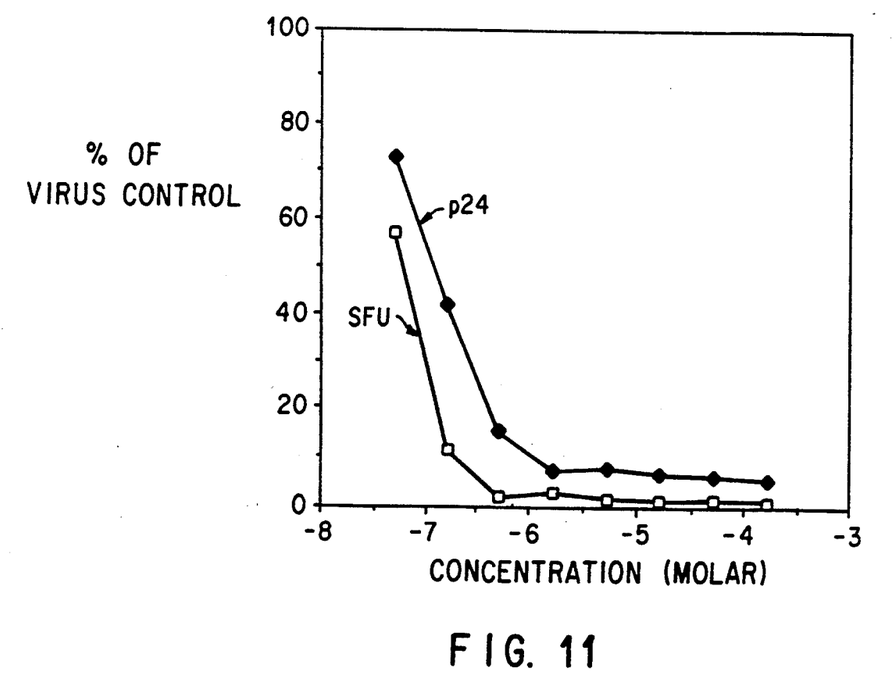

The meaning of the various dotted lines is indicated under the first diagram.

The figures from 8 to 11 illustrate the antiviral activity of the compound XXII with particular reference to cytoprotection and effect on p 24 and infectious virus synthesis.

We claim:

1. 1-phenyl substituted-1H,3H-thiazole [3,4-a] benzimidazoles having inhibitory activity against HIV-I virus, selected from the group consisting of: 1-(2-fluorophenyl)-1H,3H-thiazole [3,4-a] benzimidazole, 1-(3-fluorophenyl)-1H,3H-thiazole [3,4-a] benzimidazole, 1-(3-hydroxyphenyl)-1H,3H-thiazole [3,4-a] benzimidazole, 1-(2,6-difluorophenyl)-1H,3H-thiazole [3,4-a] benzimidazole, 1-(2,6-dichlorophenyl)-1H,3H-thiazole [3,4-a] benzimidazole, 1-(2-chloro-6-fluorophenyl)-1H,3H-thiazole [3,4-a] benzimidazole, 1-(2-chloro-5-nitrophenyl)-1H,3H-thiazole [3,4-a] benzimidazole, 1-(3-cyanophenyl)-1H,3H-thiazole [3,4-a] benzimidazole and 1-(2-nitrophenyl)-1H,3H-thiazole [3,4-a] benzimidazole.

2. A benzimidazole according to claim 1 being 1-(2-fluorophenyl)-1H,3H-thiazole [3,4-a] benzimidazole.

3. A benzimidazole according to claim 1 being 1-(3-fluorophenyl)-1H,3H-thiazole [3,4-a] benzimidazole.

4. A benzimidazole according to claim 1 being 1-(3-hydroxyphenyl)-1H,3H-thiazole [3,4-a] benzimidazole.

5. A benzimidazole according to claim 1 being 1-(2,6-difluorophenyl)-1H,3H-thiazole [3,4-a] benzimidazole.

6. A benzimidazole according to claim 1 being 1-(2,6-dichlorophenyl)-1H,3H-thiazole [3,4-a] benzimidazole.

7. A benzimidazole according to claim 1 being 1-(2-chloro-6-fluorophenyl)-1H,3H-thiazole [3,4-a] benzimidazole.

8. A benzimidazole according to claim 1 being 1-(2-chloro-5-nitrophenyl)-1H,3H-thiazole [3,4-a] benzimidazole.

9. A benzimidazole according to claim 1 being 1-(3-cyanophenyl)-1H,3H-thiazole [3,4-a] benzimidazole.

10. A benzimidazole according to claim 1 being 1-(2-nitrophenyl)-1H,3H-thiazole [3,4-a] benzimidazole.

11. Pharmaceutical compositions having inhibitory activity against HIV-1 virus comprising a therapeutically effective amount of a compound as defined in claim 1 and a suitable carrier therefor.

12. Therapeutic method for the treatment of HIV-1 virus infections comprising administering an HIV-1 virus infection treating effective dose of at least one compound according to claim 1.

* * * * *